United States Patent [19]

Maita et al.

[11] Patent Number: 4,993,941
[45] Date of Patent: Feb. 19, 1991

[54] DENTAL IRRIGATING NEEDLE

[75] Inventors: Eikichi Maita, Sendai; Kohji Ikeda, Osaka; Akira Tsuji, Kishiwada, all of Japan

[73] Assignees: Nissho Corporation; Fujisawa Pharmaceutical Co., Ltd., both of Osaka, Japan

[21] Appl. No.: 187,750

[22] Filed: Apr. 29, 1988

[30] Foreign Application Priority Data

May 7, 1987 [JP] Japan ................................. 62-111236

[51] Int. Cl.⁵ .............................................. A61G 17/02
[52] U.S. Cl. ........................................ 433/80; 604/281
[58] Field of Search ................... 433/80, 81; 604/281, 604/275, 264

[56] References Cited

U.S. PATENT DOCUMENTS

| | | | |
|---|---|---|---|
| 2,850,014 | 9/1958 | Ginsburg | 604/272 |
| 2,922,420 | 1/1960 | Cheng | 604/272 |
| 3,035,351 | 5/1962 | Hirsch | 433/224 |
| 3,330,268 | 7/1967 | Goldsmith | 604/272 |
| 3,439,675 | 4/1969 | Cohen | 604/275 |
| 3,525,339 | 8/1970 | Halligan | 604/264 |
| 3,816,921 | 6/1974 | Malmin | 433/81 |
| 3,890,977 | 6/1975 | Wilson | 604/281 |
| 3,958,557 | 5/1976 | Sharp et al. | 604/280 |
| 4,026,025 | 5/1977 | Hunt | 433/80 |
| 4,044,468 | 8/1977 | Kahn | 433/102 |
| 4,236,520 | 12/1980 | Anderson | 604/264 |
| 4,276,880 | 7/1981 | Malmin | 433/80 |
| 4,432,758 | 2/1984 | Finegold | 604/264 |
| 4,747,827 | 5/1988 | Micek | 604/281 |
| 4,813,928 | 3/1989 | Abe et al. | 604/275 |

FOREIGN PATENT DOCUMENTS 49-14471 4/1974 Japan .
62-172408 11/1987 Japan .
2143497 2/1985 United Kingdom .

Primary Examiner—Gene Mancene
Assistant Examiner—Adriene B. Lepiane
Attorney, Agent, or Firm—Oblon, Spivak, MaClelland, Maier & Neustadt

[57] ABSTRACT

A dental irrigation needle includes a hub engagable with a syringe and a cannula having one closed end and another end fitted to the hub, the cannula being formed of a freely bendable material such as annealed stainless steel. One or more nozzle orifices are formed in a lateral wall of the cannula adjacent the closed end so that a fluid from the syringe may be discharged through the nozzle orifices during the irrigation of a reamed root canal. The orifices are mutually axially and circumferentially spaced along the cannula and a marking may be provided on the hub to indicate a direction of each of the nozzle openings.

4 Claims, 1 Drawing Sheet

DENTAL IRRIGATING NEEDLE

BACKGROUND OF THE INVENTION

1. Field of the Invention

This invention relates to an irrigating needle for removing reaming chips of dentine and residual organic matter produced in the process of root canal reformation in dental treatment, and has its application in the field of health care.

2. Background of the Related Art

The dental irrigating needle (hereinafter referred to as an irrigating needle) is engaged to a syringe containing a cleansing solution in such applications as the irrigating of the canalis radicis dentis which is performed for removing reaming chips of dentine and residual organic matter produced in the process of root canal reformation. In use, the tip of the needle is applied to the irrigation site and the cleansing solution is spouted from the tip.

The conventional irrigating needle comprising a straight cannula having a nozzle orifice at its tip has proved inconvenient because the handling angle of the syringe must be delicately controlled according to the position of the tooth to be treated, the depth of the site to be irrigated, and so on.

To overcome this inconvenience, an irrigating needle comprising a cannula bent at a given angle in a position about 1 cm away from its tip has been developed and used.

However, there is also the problem that when the cleansing solution is spouted directly into the reamed tooth bottom, the reaming chips tend to enter into the tiny gaps in the bottom of the root canal and cannot be removed.

To overcome the above disadvantage, an irrigating needle provided with an orifice for spouting the cleansing solution at the lateral wall of a forward portion of the cannula has been developed and put to use.

Of the above-mentioned prior art, the former is not as satisfactory as desired because, although the bent cannula assures a greater ease of use as compared with the straight construction, the fixed bending angle is not sufficient for handling. Furthermore, since this irrigating needle is provided with a nozzle orifice at the tip of the cannula, chips of dentine and other matter cannot be fully removed as mentioned above.

In the latter of the above-mentioned prior art, the cannula of the needle is straight and not bendable so that the above-mentioned inconvenience in use remains yet be resolved.

SUMMARY OF THE INVENTION

Having as its object a solution to the above problems, this invention provides a dental irrigating needle comprising a hub adapted to be engaged to a syringe and a cannula which is made of freely bendable metal and having a closed tip and at least one nozzle orifice for spouting of the cleansing solution at the lateral wall of a forward portion of the cannula.

DETAILED DESCRIPTION OF THE PREFERRED EMBODIMENT

This invention is described below with reference to an embodiment thereof as depicted in the accompanying drawing.

Figure 1:
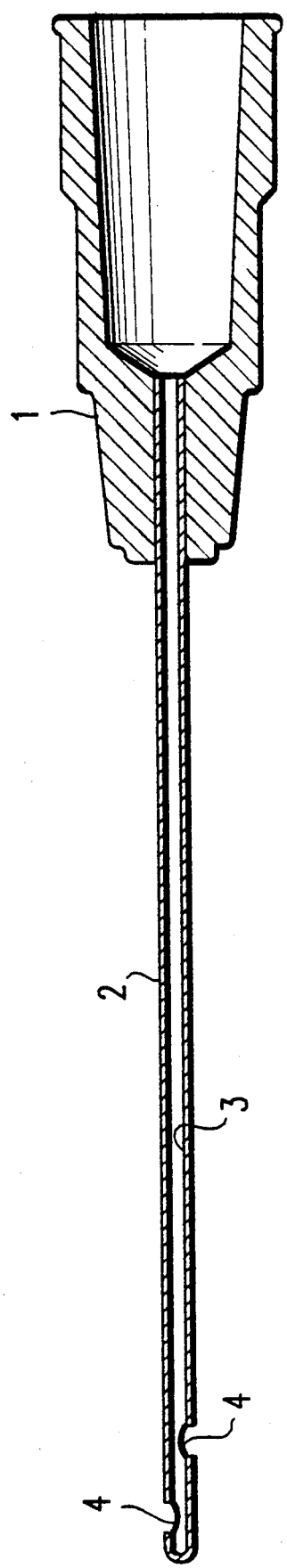
FIG. 1 is a longitudinal section view showing the irrigating needle of this invention.

FIG. 1 is a longitudinal section view showing an irrigating needle of the invention which comprises a hub (1) and a cannula (2). The hub (1) may be the same as that of the conventional needle in size, shape, material and so forth.

The cannula (2) is made of freely bendable, i.e., plastically deformable, metal and has an internal passageway (3) for the cleansing solution with its forward end closed and a couple of nozzle orifices (4,4) for spouting the cleansing solution at the lateral wall adjacent to the closed tip in longitudinally different positions, one on one side and the other on the diametrically opposite side.

The freely bendable cannula (2) of the irrigating needle of the invention can be easily provided, for example by annealing a stainless steel tube by the method described in Japanese Utility Model Publication No. 172408/1987. The tip closure of the cannula (2) can be formed by gradual inward bending of the lateral wall of the tip portion of the pre-annealed needle. On the other hand, the nozzle orifice (4) can be formed by drilling the lateral wall adjacent to the closed tip of the pre-annealed cannula (2).

Like the conventional irrigating needle, the irrigating needle of this invention is used while engaged to the tip of a syringe containing a cleansing solution such as 10% sodium hypochlorite, 3% hydrogen peroxide and other solutions.

The irrigating needle according to this invention is not limited to the above embodiment but can be provided in an optional design in respect to the length and size of the cannula, the configuration and size of the nozzle orifices, and other details.

There is no particular limitation on the number of available nozzle orifices but the arrangement of 2 or 3 orifices for spouting of the cleansing solution in diverse directions contributes to an enhanced irrigating effect and is preferable.

Furthermore, the provision of the hub with a marking indicating the direction of the nozzle orifices, such as a dot marks 5, is further convenient for use.

Figure 2:
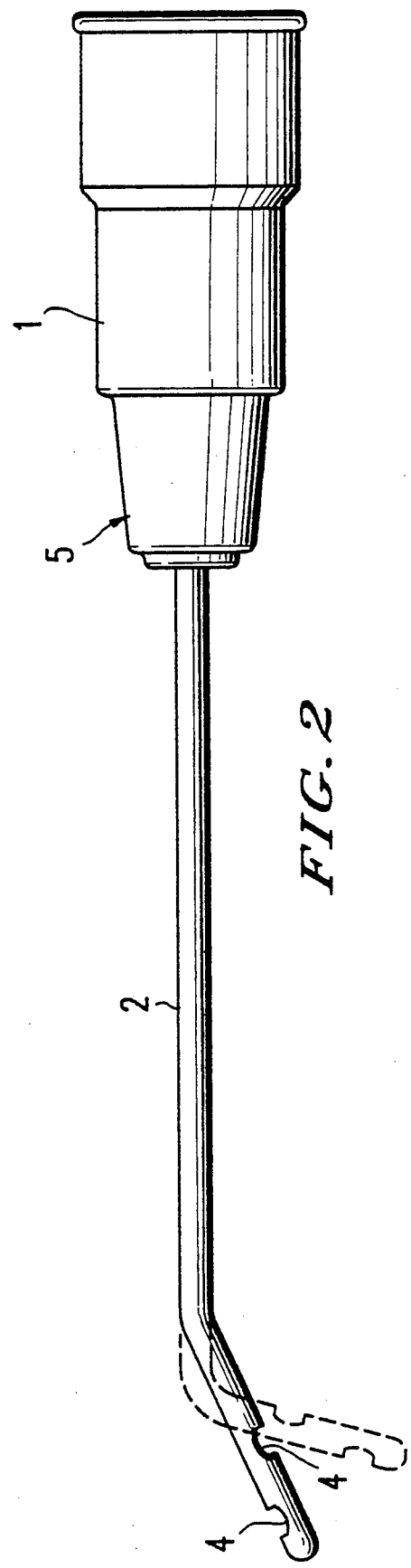
FIG. 2 is a side elevation view showing the needle in use.

Since the irrigating needle of this invention is made of freely bendable metal, it can be bent in any desired position and direction at an optional angle according to the site to be irrigated, as shown in solid and dotted lines in FIG. 2, and, moreover, can be easily inserted into a curved root canal. Thus, this irrigating needle is very convenient for use.

Furthermore, when each of plural nozzle orifices for the cleansing solution are provided on different lateral sides, the cleansing solution is spouted in different directions at the same time, so a high irrigating efficiency is obtained.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the U.S. is:

1. A dental irrigation needle comprising:

a hub having means engageable with a syringe;
a cannula having one closed end and another end fitted to the hub, said cannula being formed of a freely bendable annealed stainless steel, whereby said cannula may be bent to a desired angle and will maintain the bent angle in the absence of a restoring force; and
at least one nozzle orifice formed in a lateral wall of said cannula adjacent said one end, whereby a fluid from a syringe may be discharged through said nozzle orifice.

2. The needle of claim 1 including at least two of said nozzle orifices, said nozzle orifices being mutually axial and circumferentially spaced along said cannula.

3. The needle of claim 2 including two diametrically opposed ones of said nozzle orifices.

4. The needle of claim 1 including a marking on said hub indicating a direction of each of said at least one nozzle orifices.

* * * * *